United States Patent
Mihaylov et al.

(10) Patent No.: US 9,989,444 B2
(45) Date of Patent: Jun. 5, 2018

(54) FLOW TIMER FOR A SAMPLING APPARATUS

(71) Applicant: Nextteq LLC, Tampa, FL (US)

(72) Inventors: Gueorgui M. Mihaylov, Virginia Beach, VA (US); Bryan I. Truex, Tampa, FL (US)

(73) Assignee: Nextteq, LLC, Tampa, FL (US)

( * ) Notice: Subject to any disclaimer, the term of this patent is extended or adjusted under 35 U.S.C. 154(b) by 115 days.

(21) Appl. No.: 14/728,367

(22) Filed: Jun. 2, 2015

(65) Prior Publication Data
US 2015/0346067 A1    Dec. 3, 2015

Related U.S. Application Data

(60) Provisional application No. 62/006,336, filed on Jun. 2, 2014.

(51) Int. Cl.
*G01N 1/24*     (2006.01)
*G01N 1/22*     (2006.01)

(52) U.S. Cl.
CPC ............. *G01N 1/24* (2013.01); *G01N 1/2273* (2013.01); *G01N 2001/2276* (2013.01)

(58) Field of Classification Search
CPC . G01N 1/24; G01N 1/2273; G01N 2001/2276
USPC ....................................... 73/864.61
See application file for complete search history.

(56) References Cited

U.S. PATENT DOCUMENTS

| | | | |
|---|---|---|---|
| 3,540,261 A | 11/1970 | Scoggins | |
| 3,604,272 A * | 9/1971 | Youngs | G01N 9/12 73/170.29 |
| 4,136,032 A * | 1/1979 | Bakken | B01J 49/75 137/599.14 |
| 6,945,127 B2 | 9/2005 | Van Netten | |
| 8,434,701 B2 | 5/2013 | Lin et al. | |
| 8,714,035 B2 | 5/2014 | Mihaylav et al. | |
| 2010/0269930 A1* | 10/2010 | Lin | B08B 5/02 137/560 |
| 2011/0202031 A1* | 8/2011 | Mihaylov | A61B 10/0096 604/408 |
| 2013/0167667 A1 | 7/2013 | Mihaylov et al. | |

OTHER PUBLICATIONS

International Search Report and Written Opinion of the International Searching Authority for Int'l Appl. No. PCT/US15/33741 completed on Aug. 25, 2015 and dated Sep. 18, 2015.

* cited by examiner

*Primary Examiner* — Natalie Huls
*Assistant Examiner* — Monica S Young
(74) *Attorney, Agent, or Firm* — Bernard G. Pike; Pike IP Law, PLLC

(57) ABSTRACT

Sampling systems provide apparatuses for obtaining and assessing the composition of a fluid, typically air. Sampling systems allow industrial hygienists to assess the risks and determine the protective equipment that should be worn by personnel entering a specific environment. In one embodiment, a sampling system comprises a sampling container that draws air into its inner volume and the sampling periods are controlled by an automatic timer valve. The automatic timer valve may comprise a rotating disk or plate that provides fluid communication from the area to be sampled to the inner volume of the sample bag when apertures are aligned with inlet tube.

14 Claims, 5 Drawing Sheets

FLOW TIMER FOR A SAMPLING APPARATUS

RELATED APPLICATIONS

This application claims priority under 35 U.S.C. 119(a) to U.S. Provisional Patent Application No. 62/006,336 filed on Jun. 2, 2014.

FIELD OF THE INVENTION

The invention relates to sampling systems and methods of sampling. In certain embodiments, the sampling system comprises means for delaying the initiation of a sampling process. In another embodiment, the sampling system comprises means for intermittently sampling and/or slowing the sample process. An embodiment of a method of sampling comprises placing a closed sampling bag system at a remote location, wherein the sample bag system comprises a sample bag with inlet and an automatic control valve connected to the inlet.

BACKGROUND

Environmental sampling and analysis is regularly performed to determine the amount of various target compounds are present an area such as a chemical facility, a laboratory, confined space, or other area which could potentially be contaminated by chemical compounds. Samples may be collected over a short sampling period of time indicating a potential "instantaneous" exposure of personnel to the compounds ("grab sample") or the sample may be collected over an extended sampling period of time to determine a potential average exposure of the personnel to the compounds over the extended sampling period of time. Conventionally, samples are typically drawn into a sample bag by a sampling pump or collected on a cassette, sorbent tube, or impinger attached to the pump.

There are basically two conventional sampling systems, direct sampling systems and indirect sampling systems. Conventional direct sampling systems comprise a pump to move the gas to be sampled into a sample container, conversely, conventional indirect sampling systems use a vacuum to expand the sampling bag to draw a gas to be sampled into the sample container.

These sampling systems are designed to relatively easily obtain an accurate whole air sample and minimize contamination of the sample during the sampling process and during storage of the sample. Most sampling systems include an inflatable sample bag used to collect and/or store air, vapor, and/or gas samples or are used to collect liquid, air, vapor, and or gas samples on a sorbent tube, cassette, impinger, or other collection media by drawing the liquid, air, vapor, and or gas sample through a sample bag inlet, the sorbent tube, cassette, and/or other collection media when the sample bag is inflated or a pump is activated.

Sampling in confined spaces provides additional concerns and difficulties. The Occupational Safety and Health Association require that in some instances before an employee enters the confined space, the atmosphere within the confined space should be tested for oxygen content, for flammable gases and vapors, and for potential toxic air contaminants.

When monitoring for entries into a confined space involving a descent that comprise a stratified environment, the atmosphere should be tested a regular distances in the direction of travel and to each side. If a sampling probe is used, the entrant's rate of progress into the confined space may have to be slowed to correspond with the sampling speed and detector.

Typically to sample in a confined space, a remote sampling tube is attached to a pump in a sample analyzer. The open end of the tube is lowered into the confined space and the pump is activated to pull a sample. There are several disadvantages with this system. For example, in this system the tube is very long and it is difficult to determine if the tube is entirely purged so that the sample being taken is representative of the environment at the end or inlet of the tube. Further, certain chemical compounds may be absorbed on the walls of the tube during the sampling process thus changing the concentration of the sampled gas as it moves through the tube to the sample bag or analytical device. Further, the tubing may comprise adsorbed compounds from previous sampling processes that are desorbed into and contaminating the current sample. In addition, when a volumetric pump is used, the sampling tube and the associated resistance can result in less sample volume being drawn into the sensing device than anticipated during the specified sampling period.

There is a need for improved means of sampling in confined spaces.

SUMMARY

Sampling systems provide an apparatus for obtaining and assessing the composition of a fluid and, in some cases, provide the concentration of target compounds present in the sample. Among other things, sampling systems allow industrial hygienists to assess the risks and determine the protective equipment that should be worn by personnel entering a specific environment. In one embodiment, a sampling system comprises a sampling container. Sampling containers comprises an inner volume defined by the walls of the container and inlet tube providing fluid communication for transporting the sample into the inner volume.

Sampling apparatuses typically comprise a sample mover that moves the sample from the environment to be sampled into the sample container. The air mover may be a reduced pressure within the sample container or a sample pump for example. The sample mover may comprise an inflating mechanism capable of increasing the inner volume, reducing pressure within the inner volume, and drawing a gas, typically air, to be sampled into the inner volume. The sample may be stored for later analysis, pushed out through a colorimetric or sorbent tube, or merely stored.

Embodiments of the sampling apparatus may comprise an automatic timer valve connected to the inlet tube. The automatic timer valve may delay initiation of the sampling process, control an intermittent sampling process over an extended period of time, provide a reproducible sampling period, and/or end a sample period.

In one embodiment, the automatic timer valve comprises a rotational device with a rotation mechanism capable of rotating an axle. The axle may have a rotation component attached to the axle. The rotation component may comprise features that interact with the inlet to the sample container or collector to initiate and end a sampling period or series of sampling periods involved in a sampling process. The axle and the rotational component may share the same an axis of rotation. As such the features on the rotational component, such as apertures defined by the rotational component, will share the same axis of rotation as the axle. The rotational component or plate may define an elongated aperture.

In one embodiment, the rotational component is connected to the axle and the rotational component comprises at least one aperture at a distance R from the axis of rotation. The sampling apparatus comprises collector with an inlet tube. The inlet tube or a tube connected to the inlet tube comprises a sealing device. The sealing device is in contact with the rotating component. The contact provides a sliding seal with a surface of the rotating component. The seal prevents flow into the sample container when the inlet is not aligned with the feature, such as an aperture, on the rotation component and fluid communication with the environment to be sampled and the inner volume of the sampling container. The sealing device comprises one of an o-ring, a gasket, or a rubber bellows.

The inlet tube is located at the same distance from the axis of rotation as the distance the aperture is from the axis of rotation. As such the inlet tube may be aligned with the aperture as the rotational component rotates. As the aperture is aligned with the opening of the sealing device or inlet tube, fluid communication is provided between the inner volume and an environment to be sampled. The rotational component is a plate and the feature, such as the apertures, may be defined in the plate. In such embodiments, the aperture rotates with the rotating plate and is capable of aligning with the inlet tube. The surface of the plate contacts the sealing device thereby sealing the inlet tube to retard sampling when the aperture is not aligned with the inlet tube.

The sampling container may comprise rigid walls such as, but not limited to, a summa container or may comprise at least one flexible wall such as the sample bags described in the patent applications that are incorporated by reference herein. The inflating system for a sample container with a flexible wall may comprise at least one of a shape memory component, a spring, a pneumatic system, a hydraulic system, and a weighted system.

The rotational component of the automatic timer valve comprises means for rotating the axle and/or the rotational component. In embodiments, the automatic timer valve comprises an electric motor, a spring operated motor or a weight operate motor. In cases where an inherently safe rotational device is required a spring operated motor or a weight operate motor may be beneficial.

The rotational speed of the rotational component and the length of the aperture or cumulative length of the apertures that the sealing device passes over during a sample process defines the total sample period. The average flow rate multiplied by the total sample period defines the sampled volume. The sampling apparatus may comprise replaceable rotating components that may interchangeably be attached to the axle or other rotating component of the rotation device. As such, the sampling apparatus may be used for various sampling processes for preset short sampling periods such as grab samples or 15 min., 30 min., 2 hrs. (STEL or Ceiling, or other task-duration periods in some occasions) and/or extended sampling periods including 8 hours to 24 hours (TWA) without use of pumps and/or auxiliary vacuum equipment.

The plurality of rotational components include rotational components that may be interchangeably connected to the axle. Each rotational component comprises at least one aperture, and wherein when the aperture is aligned with the inlet tube fluid communication is provided between the inner volume and an environment to be sampled.

The plurality of rotational components comprise a first rotational component and a second rotational component and the first rotational component comprises a first pattern of apertures and the second rotational component comprises a second pattern of apertures, wherein the first pattern of apertures is different than the second pattern of apertures.

In embodiments, the rotational device may rotates the rotating plate at any desired rate such as, but not limited to, between once per hour and 10 times per minute (once per six seconds), in other embodiments, the rotating rotates the rotating component or plate between once per 30 minutes and 2 times per minute. In still further embodiments, the means for rotating rotates the rotating plate about 1 time per 15 minutes. In some embodiments, the aperture aligns with the inlet tube to allow sampling once per rotation of the plate.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

BRIEF DESCRIPTION OF THE DRAWINGS

FIG. 1B depicts the sampling apparatus of FIG. 1B after the sampling process comprising rotation of the rotational component and alignment of apertures on the rotating disk with an opening in the sealing device 114a; FIG. 1C depicts a plan view of the sealing device of FIG. 1D.

DESCRIPTION

Figure 1A:
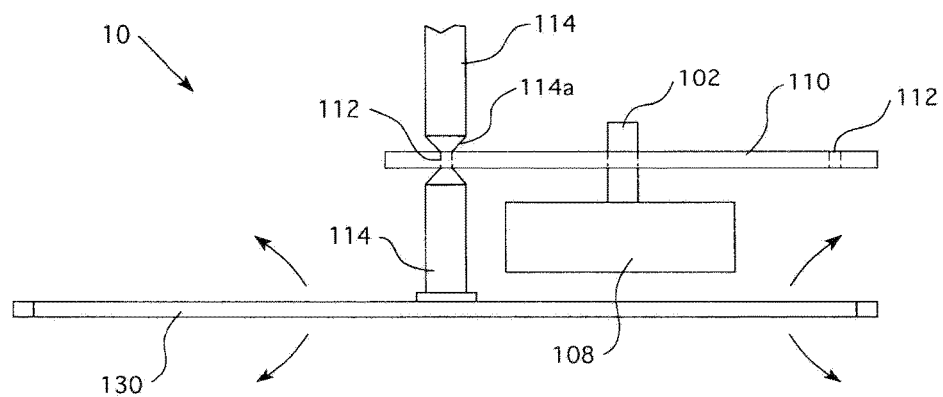
FIG. 1A depicts an embodiment of a sampling apparatus comprising a rotating disk, a stationary inlet tube, automatic timer valve, and sample container in the initial configuration wherein the sample container does not comprise a sample.
Figure 1B:
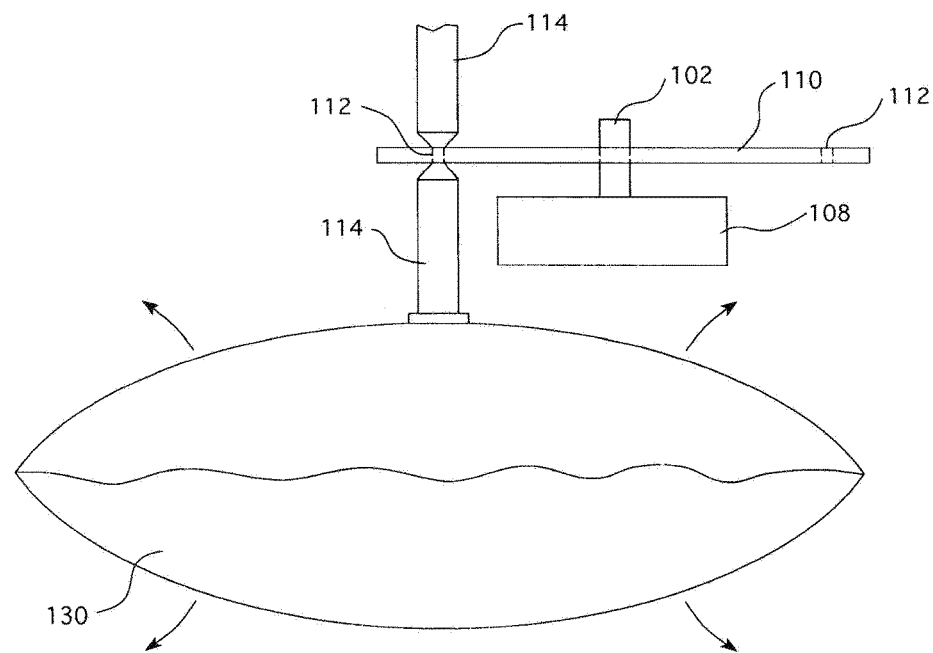

Embodiments include sampling systems, sampling valve mechanisms, and methods of sampling. In addition to other samples, additionally whole air samples may be obtained with specific embodiments of the sampling systems, sampling valve mechanisms, and method of sampling.

Whole air samples are taken over a period of time to determine the concentrations of one or more target compounds present in the environment during that period of time and determine the approximate average concentration of target compounds in the air over that period of time.

Further, sampling and monitoring methods may generally be described as manual or automated methods. A manual method of the sampling and monitoring requires two distinct steps: sample collection into a sample container such as, but not limited to, a sample bag or a canister, followed by sample analysis to determine concentration of at least one target compound or contaminant in the collected sample. The contaminant may be either separated from the sample gas stream during the sampling process, as is often done when collecting suspended particulate matter, such on a filter, or a "whole air" sample may be collected without contaminant separation from the sample gas. Capturing a "whole air" sample is one of the primary methods for sampling for the presence of volatile organic compounds in ambient air or in confined spaces. Conversely, automated methods employ instruments, such as portable gas chromatographs, which are capable of performing the sampling and analysis of the certain target contaminants in real time or near-real time.

"Whole air" sampling involves collecting a sample for analysis and includes both grab sampling and integrated sampling. Both methods may use containers made of stainless steel (e.g., passivated canisters), glass, or pliable plastics (such as, but not limited to, polyethylene Terephthalate (Mylar®), polyvinyl fluoride (Tedlar®), polytetrafluoroethylene (Teflon®), aluminized polyvinyl chloride (PVC), and stainless steel, for example, to collect and retain the sample. The "whole air" sample may be drawn through a sampling train comprised of components that regulate the flow rate and duration of the sampling process such as a self-sampling bag and an embodiment of the automatic timer valve.

An embodiment of the sampling apparatus includes, but is not limited to, a collector that contains and has an inner surface will be in contact with the sample. The collector should be, or should have an inner surface that is sufficiently inert to the target compounds and other components in the sample, does not desorb or absorb any target compounds or other compounds that results in substantially affecting the analytical results by adding contaminants to the sample, reacting with the components of the sample, or by absorbing a portion of the sample. If an air mover and flow measuring device or remote sample tubing are placed before the collection step, then parts of those devices contacting the sample stream must also be substantially inert to the target gases so as to not add or remove target compounds, contaminants, or other components of the sample.

Air sampling is becoming more important in recent years due to research indicating that there are certain measureable health effects associated with even small quantities of toxics in the air, promulgation of air toxic regulations by state air pollution agencies, and improvements in analytical techniques which allow ever-increasingly smaller quantities of pollutants to be detected at a reasonable cost. The ability to assess the environmental conditions for personnel should not be adversely affected by the components of the sampling system or train used to obtain the sample.

Mechanisms used to move air through the sample apparatus components and measure the quantity of air are integral parts of sampling trains. Conventional air movers are typically motor-driven pumps. Additionally, when motor-driven pumps are not practical, ejectors, displacement methods such as pistons, evacuated canisters, or other volumetric pumps can be used.

However, alternative air movers have been disclosed in U.S. patent application Ser. Nos. 13/729,533; 13/028,620; and Ser. No. 13/028,587, all of which are hereby incorporated by reference in their entirety. Embodiments of the systems and devices described in these applications operate by creating a vacuum within the inner volume of the sample bag to draw a sample into the sample bag. In some embodiments, the systems and methods create the slight vacuum with the inner volume of the sample bag by pulling the walls of the sample bag apart such as a vacuum of 1 to 5 inches of water. The weight of such sampling systems and sampling bags is an order of magnitude smaller than the other conventional sampling systems and devices at approximately 80 to 200 grams for 1.2 liter to 5 liter of sampling volume. These features make them applicable for sampling in remote or confined spaces such as through manholes, silos, channels, tanks, and other confined spaces.

Embodiments of the sampling systems and sampling devices of the incorporated patent applications may be considered to be self-sampling devices. As used herein, a self-sampling device may be placed in a location and allowed to "self-inflate" over a period of time, the self-inflating may be performed by agile walls, a shape memory component, a weighted sampling bag or weighted sample bag container, springs, pneumatic or hydraulic cylinders, as well as other self-inflating devices. After the sample bag is inflated with the sample including the target gases, it may be collected and sent for analysis.

Embodiments of the sampling system may comprise a self-sampling device comprising an inlet and a sampling control valve or automatic timer valve connected to the inlet. The automatic timer valve mechanism may extend the sampling time of the unrestricted self-sampling device. The automatic timer valve mechanism may also delay the initiation of the sampling process.

For confined space sampling, there should not be any personnel entry into the confined space prior to sampling to confirm an acceptable atmosphere is available, the sampling apparatus or a portion of the sampling apparatus may have to be lowered through a manway or manhole into the confined space to a targeted location(s) to properly sample the atmosphere at that location. To obtain an appropriate sample, the sampling process should not be initiated or the flow of the sampling process should be restricted until the inlet of the sampling apparatus or sampling device is located in the targeted location. For example, if the sampling period is three minutes, the introduction of the sample device fifty feet into the confined space may comprise thirty seconds of travel time to the sampling location and, thus, may introduce a significant error in the concentration of targeted compounds in the collected sample. For example, if the composition of the gas is stratified or the concentrations of gases are otherwise heterogeneous throughout the confined space the sample gas may not represent the target location(s). Gases may stratify in a confined space due to density differences between the gases, due to varied distances from a source of the contaminant, and/or gas flows within or into the confined spaces, for example. To counteract these differences in gas concentrations, the flow into the sample bag during the sampling process may be restricted and the sampling process lengthened to dilute the effects of positioning the sample bag. For example, if the sampling process for the self-sampling apparatus and the automatic timer valve may extend the sampling period to several minutes to reduce the dilution effect occurring while the sample device is lowered into the targeted location of the sampling environment.

One embodiment of a sampling valve mechanism may comprise a rotation device, such as a motor including electric and spring driven, clock mechanisms or other clock-like mechanisms. Like a standard clock mechanism, the rotation device may comprise two or more rotating axles such that one complete rotation is completed by each axle in different times. Using the clock mechanism as an example, one axle may complete a rotation in one minute and the other axle may complete a rotation in one hour. Other embodiments of a rotation device, including single axle rotational devices, may be configured for other rotation times, for example, a complete rotation in 10 second, 15 seconds, 20 seconds, 30 seconds, 45 seconds, one minute, two minutes, five minutes, ten minutes, eight hours, or other complete rotation period. In still other embodiments of the rotation device, the axles do not make a complete rotation or nearly complete rotation but the entire sampling process is completed with only a partial rotation such as, but not limited to, 45°, 90°, 135°, and/or 180° rotations.

The sampling valve mechanism may comprise a rotating component connected to an axle, pivot, or other rotating element of the rotation device. The rotating component will have a sealing contact with an inlet to the sample bag. The rotating component will have features capable of controlling, initiating and/or stopping the flow of a sample into the sample bag by opening or closing the inlet to the sample bag. To close the inlet, the rotating component may comprise a seal or may be formed from a material capable of sealing the inlet to the sample bag. The rotating disk may also comprise a material with a low coefficient of friction to facilitate rotation of the rotating component. The rotating component may be a rotating disk, a partial disk or other shape, for example. The disk may comprise polytetrafluoroethylene, at least one surface of polytetrafluoroethylene, or a top and bottom surface of polytetrafluoroethylene, for example, because polytetrafluoroethylene has adequate sealing properties with other materials, sufficiently low coefficient of friction, and is substantially inert in most sampling conditions. Particularly, the sealing portion of the rotating component or any component in contact with the inlet tube or connector to the inlet tube may be made of Teflon or a similar material with appropriate properties.

An embodiment of a sampling system, sampling apparatus, or sampling, device comprising an automatic timer valve 10 is shown in FIG. 1. The automatic timer valve controls the intake of a sample from an air to be sampled into the inner volume of a sample bag. The automatic timer valve controls the fluid communication between the inner volume and the area to be sampled. For example, the automatic timer valve 10 comprises a rotation device 108 that drives a rotating axle 102. The rotation device 108 may be powered by any energy source such as, but not limited to, direct electrical power, batteries, springs, or other energy storage device within the rotational device 108. A rotating component 110 is permanently or releasably mounted on the rotating axle 102. The rotating component comprise features that control or define the sampling process. The features rotate past the inlet and provide or prevent fluid communication between the inner volume and the area to be sampled.

Figure 5:
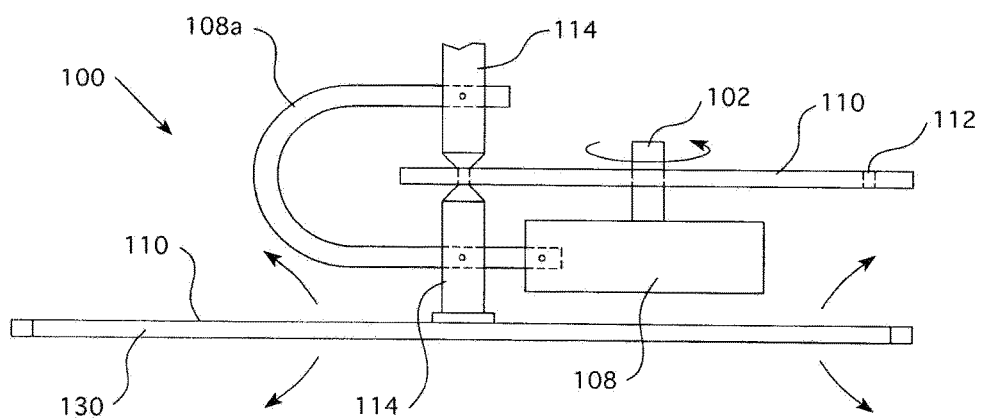
FIG. 5 depicts the embodiment of the sampling apparatus depicting a bracket securing the inlet tube and/or sealing device stationary relative to the rotational device.

The automatic timer valve further comprises an inlet tube 114 mounted stationary to the rotational device 108 (See bracket 108a in FIG. 5) such that the rotating component rotates relative to the inlet tube 114 and the housing of the rotation device 108. The inlet tube 114 is shown generally and may comprise additional components such as connectors and/or replaceable tips or seals, for example, see FIGS. 1C, 1D, and 1E. The inlet tube 114 is mounted such that the inlet tube 114 forms an effective seal when in contact with a solid surface of the rotating component 110. The inlet tubes 114 may form and effective sliding seal between the top and bottom surface of the rotating component 110. As the rotating component rotates and an aperture 112 defined in the face of the rotating component 110 aligns with the inlet tube 114, an inner volume of a sampling bag 130 attached to the inlet tube 114 becomes in fluid communication with an environment to be sampled resulting in a sample fluid being drawn into the inner volume of the sample bag. The sampling bag or other collector may be under negative pressure or may be connected to the inlet of a sample pump. As the rotating component 110 continues to rotate, the surface of the rotating component 110 may again seal the inlet tube 114 blocking fluid communication between the environment and the sample bag 130, substantially stopping further sampling either completely or temporarily based upon the sampling profile of features of the rotating component and the properties of the rotation mechanism. FIG. 1A depicts the sampling apparatus 10 prior to initiation of the sampling process. The sample bag 130 may be an air mover such as those described in the patent referenced above or could be replaced with a sample pump discharging into a sample bag. At initiation, the sealing device 114a on the inlet line 114 is in contact with the top and bottom surfaces of the rotating component 110. As the rotating component 110 is rotated by the rotation device 108 and aperture 112 defined in the rotating component 108 will align with an opening in the sealing device 114 providing fluid communication between the area to be sampled and the inner volume of the sample collector 130. In the embodiment shown in FIGS. 1A and 1B, the sample bag undergoes a biasing force (as shown by the arrows) expanding the inner volume to create a reduced pressure with the collector 130. The reduced pressure results in a fluid sample being drawn into the inner volume for the period when the aperture 112 is aligned with the inlet tube 114 providing fluid communication between the area to be sampled and the inner volume of the sample collector 130. The inlet tube 114 may comprise two sections, for example, a first section between the sample bag inlet and the bottom surface of the rotating component 110 and a second section contacting an upper surface of the rotating component 110 and extending to the area to be sampled. In other embodiments, the inlet tube may consist of the first section between the sample bag inlet and the bottom surface of the rotating component 110. The rotating component 110 continues to rotate resulting in the end of the sampling period or the end of one sampling period and after continued rotation the beginning of another sampling period in the case of intermittent sampling. Typically, the rotational device will rotate from an initial position wherein the surface of the rotational device 110 closes the inlet 114 of the sample bag by sealing contact to a final position wherein the surface of the rotational device 110 again closes the inlet 114 of the sample bag by sealing contact. In between the initial position and the final position, the features such as apertures defined in the surface of the rotating component 110, for example, provide fluid communication between the area to be sampled and the inner volume of the sample bag 130.

Figure 2A:
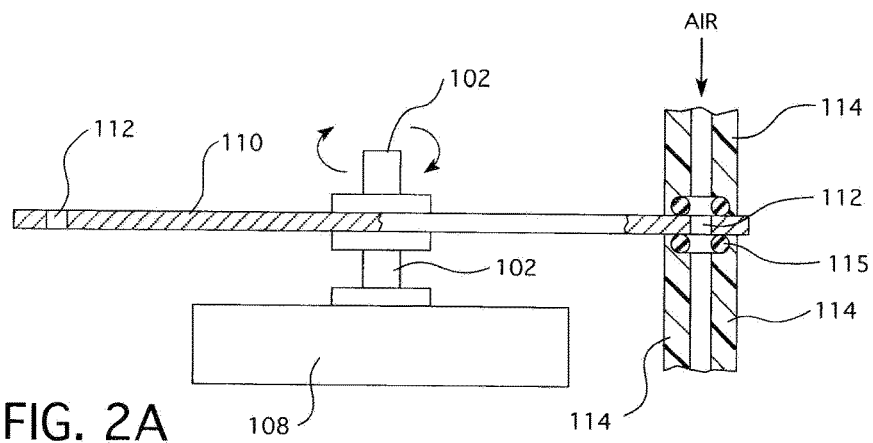
FIG. 2A depicts an embodiment of components of sampling apparatus comprising a sampling valve mechanism comprising rotation disk and stationary inlet tube.
Figure 2B:
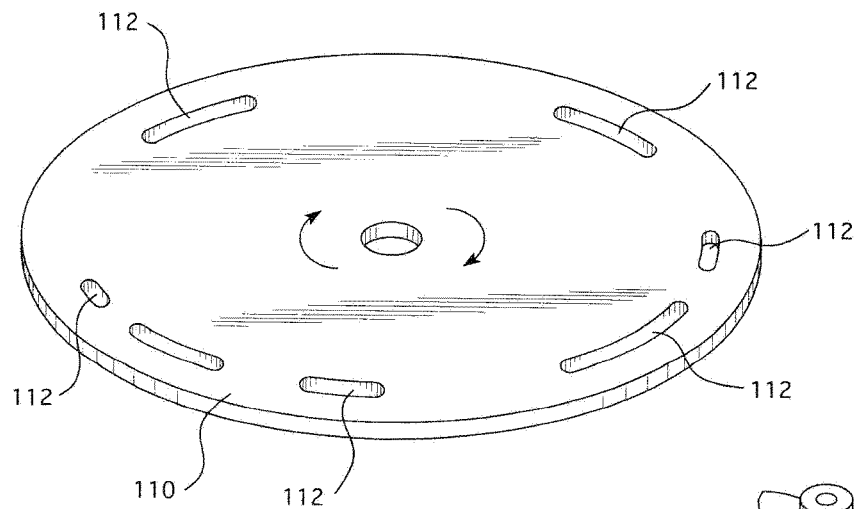
FIG. 2B shows a perspective view of the rotating disk.
Figure 2C:
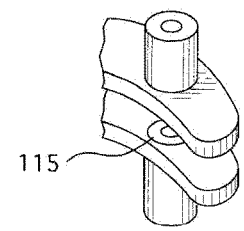
FIG. 2C depicts a perspective view of the sealing device comprising extensions that seal an elongated aperture.
Figure 3A:
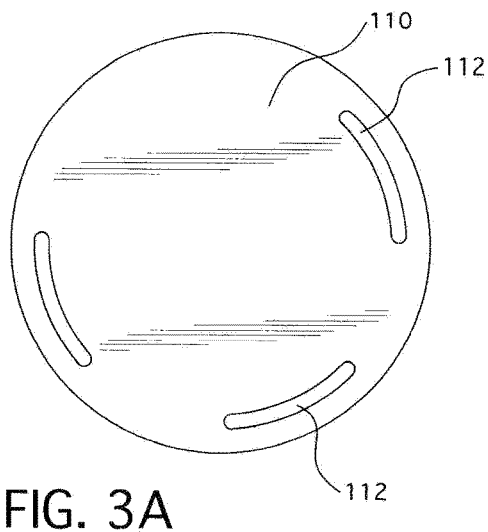
FIGS. 3a, 3b, 3c, and 3d depict embodiments of rotating disk that may be interchangeably attached to the sampling apparatus to change the characteristics of the sampling process.
Figure 3B:
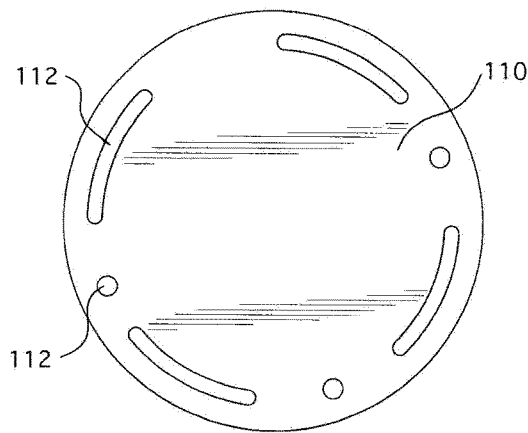
Figure 3C:
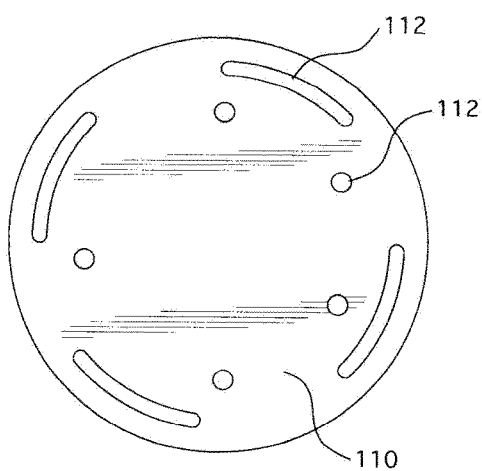
Figure 3D:
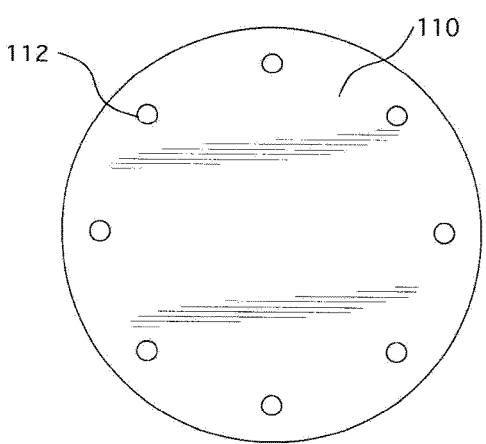

Another embodiment of the automatic timer valve is shown in FIGS. 2A, 2B and 2C, for example. In this embodiment, the rotating component 110 defines a plurality of apertures 112 allowing a plurality of sampling periods as the rotating component 110 rotates through the entire sampling process from the initial position to the final position. The aperture 112a is a short aperture and provides a short sampling time compared to aperture 112b which is an elongated aperture located a constant radial distance from the axis of rotation of the rotating component 110. The aperture 112b may be sized relative to the speed of rotation of the rotating component 110. The sampling period may be calculated by dividing the length of the angle from the beginning of the aperture to the end of the aperture by 360 degrees and multiplying the result of this calculation by the time for one complete rotation of the rotating component. For example, if the aperture extends through 120 degrees of rotation and the time of one complete rotation of the rotating component is three minutes, the sample period would be one minute. Another embodiment of the rotating component may comprise a plurality of apertures 112. The plurality of apertures would take samples at a plurality of sample periods based upon the angular distance between the apertures and would allow sampling for a period based upon the size of the aperture.

An embodiment of the automatic timer valve may comprise a plurality of interchangeable rotating components that define different sampling period characteristics. The embodiments of the rotating components 110 shown in FIGS. 3a, 3b, 3c and 3d are in the shape of a disk, but other embodiments may have different shapes. Each of the embodiments in these figures have a different aperture pattern and, therefore, a different sampling flow pattern. The sample flows into the sample bag when the apertures defined in the rotating disk are aligned with the opening in the sealing device 114a of the inlet 114. The embodiment of the rotating component in FIG. 5a comprises three elongated apertures 112 to provide three periods of intermittent sampling periods over a complete revolution of the rotating component 110. The three periods are of similar duration and evenly spaced. The embodiment of the rotating component in FIG. 5b comprises three pairs of apertures comprising a circular short aperture and an elongated aperture 112 to provide three periods of intermittent sampling over a complete revolution of the rotating component 110 from the initial position to the final position. The pairs of apertures provide a blend of short periods and longer periods of sampling. The embodiment of the rotating component in FIG. 5c has two sampling rings spaced at different radii from the axis of rotation of the rotating component 110. The inlet 114 and/or sealing device 114a may be moved to align with either the inner ring or the outer ring of features providing two different sampling processes on one rotating component. The inner ring provides five circular apertures 112 to provide intermittent short interval sampling periods. The outer ring provides four elongated apertures 112 to provide four intermittent periods of sampling. The total length of the apertures between the initial position and the final position and the rotation speed of the rotating disk define the total sampling period. In the embodiment shown in FIG. 3c, the outer ring of apertures will provide a total sampling period that is approximately one half of the time that the rotating disk would complete one complete revolution from the initial position to the final position in an embodiment wherein the rotating device is capable of completing one revolution. The total sampling period may double if the rotating component 110 would complete two rotations over the apertures 112. Other embodiments may include multiple rotations of the rotating component over the inlet 114. The number of rotations may be preprogrammed into the rotational device 108 or may depend on the number of times that the spring is wound prior to initiation of the sample process, for example. The inner ring of apertures would provide five short sampling periods. The embodiment of the rotating component in FIG. 5d comprises eight circular apertures 112 to provide eight periods of intermittent sampling over a complete revolution of the rotating component 110 from the initial position to the final position.

Figure 1C:
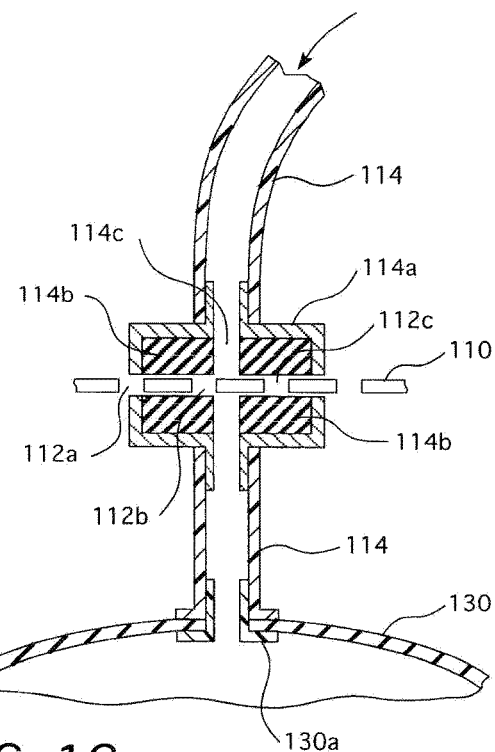
FIG. 1C depicts an enlarged view of an embodiment of the rotating disk with the sealing device.
Figure 1D:
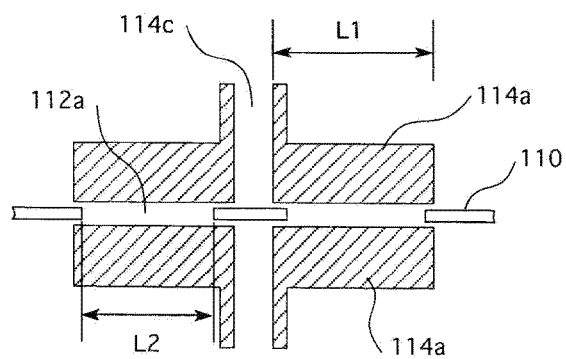
FIG. 1D depicts an enlarged view of another embodiment of the rotating disk with the sealing device for elongated apertures in the rotating disk.
Figure 1E:
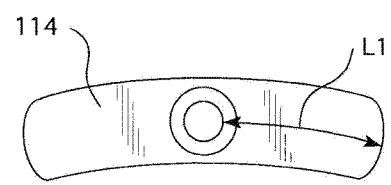
FIG. 1E depicts an elongated sealing device for sealing elongated apertures in the rotating component.

FIGS. 1C and 1D show enlarged views of embodiments of the sliding seal components of the timer valve. In the embodiment of FIG. 1D, the inlet tube 114 is slidingly connected to seal on both the top and bottom surfaces of the rotating component 110. At the end of the inlet tubes 114 is a sealing device 114a sealing connected to the inlet tube 114 on each side of the rotating component 110. The sealing device 114a comprises a seal 114b for the top and bottom surfaces of the rotating component 110. In the position shown in FIG. 1D of the rotating component 110, aperture 112b has passed by the opening 114c defined in the seal 114b. Apertures 112b and 112c are shown within the sealing area of the seal 114b. Thus, as shown the timer valve of FIG. 1D is in the closed position. In the closed position, the timer valve does not provide fluid communication between the environment to be sampled and the inner volume of the sample bag 130. As the rotating component 110 further rotates, aperture 112c will move out from between the seals 114b and into the opening in the seals 114b to an opened position wherein the timer valve provides fluid communication between the environment to be sampled and the inner volume of the sample bag 130. In this manner, the timer valve may provide intermittent sampling of the environment over a period of time. The embodiment of the sealing device 114a of FIG. 1D comprises replaceable seals. The replaceable seals may be removed from the housing and replaced is the seals are worn or begin to leak. Another embodiment of the sealing device of a timer valve is shown in FIG. 1E, the sealing device 114a comprises two solid pieces of a sealing material. Such an embodiment of the sealing device may comprise Teflon. The apertures 112a are defined in rotating component 110. The seals have a seal length between the inner edge and the outer edge L1 and the apertures have an aperture length L2. The seal length L2 is greater than the aperture length such that as the aperture enters the opening 114c of the seal 114a, the timer valve provides fluid communication through the inlet tube 114 to the area to be sampled and prevents leaking of gas around the sealing device. The length of the aperture L2 and the rotational speed of the rotating component define the continuous sample period of the timer valve for a single aperture. The entire sample period is defined by the entire series of apertures and is the total of each of the individual continuous sample periods.

Figure 4:
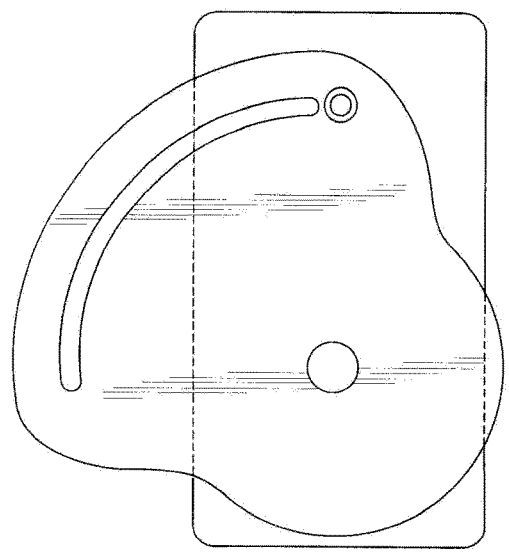
FIG. 4 depicts another embodiment of the rotating component with a single elongated aperture.

The sampling apparatus may comprise a plurality of rotational components that may be interchangeably connected to an axle of the rotational device. The plurality of rotational components may comprise a first rotational component and a second rotational component, for example. The first rotational component comprises a first pattern of apertures and the second rotational component comprises a second pattern of apertures, wherein the first pattern of apertures is different than the second pattern of apertures. The rotational components may be interchanged to provide different sampling periods for the sampling apparatus Further embodiments of the rotating component is shown in FIG. 4. This embodiment of the rotating component 110 may be used with a rotation device 108 wherein the axle or axles do not travel a complete rotation. In some embodiments of the sampling device, the rotation components only travel a portion of the complete rotation. In the embodiment of the rotating component 110 of FIG. 4, the rotating component 110 moves approximately through a ninety degree rotation from the initial position to the final position. In this embodiment, the sampling process comprises an initial delay period from T0 to T1, a sample period from T1 to T2, and a shut off period T2 to T3 wherein no further sampling occurs. The length of each period may be modified by location, number, and length of the aperture 112 or use of the rotating component 100 FIG. 3 with rotation devices with differing rotational speeds.

The size, time, and frequency when an aperture is aligned with the inlet tube opening defines the particular sample time for a rotating component and rotating disk combination. In some embodiments, the rotating component may comprise apertures of varying angular lengths or widths. The total sampling volume would be a function of the sampling flow rate of the self-sampling device and the total sampling period of each of the apertures. For example, the rotating component may comprise four apertures, a first aperture allowing a one minute sample period, second aperture allowing a five minute sample period, third aperture allowing a five minute sample period, and a fourth aperture allowing a ten minute sample period. Additional or fewer apertures may be provided in other embodiments.

Additionally, in certain embodiments, the rotational component of the automatic timer valve may complete more than one rotation relative to the inlet. Therefore, the sampling may occur for a certain period of time for multiple repetitions until the desired amount of sample gas is obtained. Thus, the sampling periods may be extended beyond a single rotation time, for example, the inlet sampling valve mechanism and mechanism may be used for twelve hour samples, twenty four hour samples, two day samples or other extended periods of time. The sample control mechanism and rotation component may be designed to provide one sampling period every twelve hours, for example.

In other embodiments, the flow timer may comprise a rotating arm and an inlet port capable of being sealed by the rotating arm. The rotating arm is connected to a rotation mechanism that may be rotated out of sealing connection with the inlet port and allowed to rotate back in sealing connection with the inlet port. The inlet port is in fluid connection with a sampling system such that sampling begins when the inlet port is open and ends when the inlet port is closed. In some embodiments the rotating arm moves consistently toward the sealing inlet during the sampling period and in other embodiments the arm will stay substantially stationary relative to the inlet port until the end of the sampling period and the arm will be released and return to seal the inlet port by a spring or other biasing force. The rotation mechanism 108 may be electrical or mechanical.

In other embodiments of the sampling device may comprise a plurality of inlet tubes situated on different or substantially similar distances from the axis of rotation of the rotation device. Each inlet tube may simultaneously or consecutively sample. The time interval between the various inlet tubes is proportional to the size of the apertures. In such embodiments, one inlet flow valve or mechanism may control the sample flow to a plurality of sampling devices and obtain samples into separate bags. Each sample bag may comprise its own valve that may be closed and retain the sample after removal from the control valve or mechanism. The sample bag may be connected to the sample control valve with a quick connector, for example, a push-to-connect fitting.

The sampling flow for a self-sampling device and other flow devices is at least partially determined by the diameter of the inlet opening. Thus, the flow rate and time length of the sampling process after an aperture is aligned defines the total volume of sampled gas. Different sized apertures at different radial distances from the axis of rotation on the same rotating component may align to different inlet tubes, thus a single rotating component may be used for different sampling periods or for multiple sample bags.

The entire sampling system using a self-sampling device and a sample control mechanism may be very light and have appropriate dimensions to be deployed in many desired environments and provide convenient and accurate sampling. Such sampling systems may be deployed in confined spaces, manholes, tanks, ship holds, etc. For control valves that include multiple sample bags that may be sampled consecutively so that a profile of the concentration of analytes may be determined at different locations and an average concentration may also be determined. For example, consecutive sampling could be achieved into two separate sample bags by using aperture 112*b* and aperture 112*c* as shown on the rotating component 110 shown in FIG. 2.

Further since the sampling system is light and, in some embodiments, does not use electrical power (a spring powered rotating axle, for example), may be deployed on a balloon, such as a weather balloon, or a remote control helicopter in open atmosphere for an environmental profile and distribution of contaminants as a function of altitude. For example, remote control quad helicopters may carry several sample bags with a single inlet flow control mechanism and thus provide information of the concentration of analytes at different altitudes. Such sampling systems may be deployed over chimneys, stacks, or other emission pipes, for example. The light weight, low power requirements, and versatility of the sampling systems open new area of scientific applications and routine operations.

Other aspects and features of embodiments of the sampling bags comprising agile walls will become apparent to those of ordinary skill in the art, upon reviewing the following description of specific, exemplary embodiments of the present invention in concert with the figures. While features may be discussed relative to certain embodiments and figures, all embodiments can include one or more of the features discussed herein. While one or more particular embodiments may be discussed herein as having certain advantageous features, each of such features may also be integrated into various other of the embodiments of the invention (except to the extent that such integration is incompatible with other features thereof) discussed herein.

In similar fashion, while exemplary embodiments may be discussed below as system or method embodiments it is to be understood that such exemplary embodiments can be implemented in various systems and methods.

The embodiments of the described methods and sampling apparatuses are not limited to the particular embodiments, method steps, and materials disclosed herein as such formulations, process steps, and materials may vary somewhat. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of the invention are described with reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

The invention claimed is:

1. A sampling system for sampling gasses, comprising:
    a sampling container; wherein the sampling container comprises an inner volume and an inlet tube;
    an inflating mechanism capable of increasing the inner volume of the sample container to create a negative pressure within the inner volume to draw in a gas to be sampled into the inner volume; and
    an automatic timer valve connected to the inlet tube, wherein the automatic timer valve comprises:
        a rotational device with a rotation mechanism capable of rotating an axle, wherein the axle has an axis of rotation; and
        a first replaceable rotational component and a second replaceable rotational component interchangeably connected to the axle, wherein the first replaceable rotational component comprises at least one first sampling aperture at a distance from the axis of rotation and the second replaceable rotational component comprises at least one second sampling aperture at a distance from the axis of rotation;
    wherein the inlet tube comprises at least one sealing device having a sliding seal in contact with a surface of either the first replaceable rotational component or the second replaceable rotational component interchangeably connected to the axle and an opening, wherein the inlet tube is located at the same distance from the axis of rotation as the aperture such that the inlet tube can align with the opening, wherein the first replaceable rotational component comprises an initial delay period, wherein the rotational device begins rotating the axle and the sealing device is in sealing contact with the first replaceable rotational component, a sampling period wherein the first sampling aperture or the second sampling aperture is aligned with the opening providing fluid communication between the inner volume of the sample container and an environment to be sampled, and an end period after the sampling period, wherein the sealing device is in sealing contact with the first replaceable rotational component or the second replaceable rotational component; and wherein the first sampling aperture is different in length than the second sampling aperture.

2. The sampling system of claim 1, wherein the sampling container comprises at least one flexible wall.

3. The sampling system of claim 1, wherein the sealing device comprises one of an o-ring, a gasket, polytetrafluoroethylene, or a rubber bellows.

4. The sampling system of claim 1, wherein the inflating system comprises at least one of a shape memory component, a spring, a pneumatic system, a hydraulic system, and a weighted system.

5. The sampling system of claim 1, wherein the automatic timer valve comprises an electric motor.

6. The sampling system of claim 1, wherein the first replaceable rotational component is a plate.

7. The sampling system of claim 6, wherein during the initial period at least one surface of the plate seals against the sealing device to prevent sampling when the aperture is not aligned with the inlet tube.

8. The sampling system of claim 6, wherein the rotational device rotates the plate at a rate in the range of once per hour and 10 times per minute.

9. The sampling system of claim 6, wherein the rotational device rotates the plate at a rate in the range of once per 30 minutes and 2 times per minute.

10. The sampling system of claim 9, wherein the rotational device rotates the rotating plate about 1 time per 15 minutes.

11. The sampling system of claim 10, wherein the aperture aligns with the inlet tube to allow sampling once per rotation of the plate from an initial position to a final position.

12. The sampling system of claim 6, wherein the plate defines an elongated aperture.

13. The sampling system of claim 1, wherein the rotational device comprises one of a spring operated motor or a weight operated motor.

14. The sampling system of claim 1, wherein the sealing device is constructed of a material capable of forming a seal with the rotating plate.

* * * * *